United States Patent
Kim

(10) Patent No.: US 11,585,765 B1
(45) Date of Patent: Feb. 21, 2023

(54) APPARATUS, METHOD, COMPUTER-READABLE STORAGE MEDIUM FOR NON-DESTRUCTIVE INSPECTION OF BICYCLE BASED ON ANALYZING AMOUNT OF SCALE VALUE CHANGE

(71) Applicant: Wrightbrothers Co., Ltd, Seoul (KR)

(72) Inventor: Hee Soo Kim, Seoul (KR)

(73) Assignee: WRIGHTBROTHERS CO., LTD, Seoul (KR)

( * ) Notice: Subject to any disclaimer, the term of this patent is extended or adjusted under 35 U.S.C. 154(b) by 0 days.

(21) Appl. No.: 17/551,627

(22) Filed: Dec. 15, 2021

(30) Foreign Application Priority Data

Sep. 16, 2021 (KR) .................. 10-2021-0123908

(51) Int. Cl.
| | |
|---|---|
| *G01N 23/04* | (2018.01) |
| *G06N 3/08* | (2006.01) |
| *G01N 23/083* | (2018.01) |
| *G06N 3/04* | (2006.01) |
| *G01N 23/18* | (2018.01) |

(52) U.S. Cl.
CPC ........... *G01N 23/04* (2013.01); *G01N 23/083* (2013.01); *G01N 23/18* (2013.01); *G06N 3/0454* (2013.01); *G06N 3/08* (2013.01)

(58) Field of Classification Search
CPC ...... G01N 23/04; G01N 23/083; G01N 23/18; G06N 3/0454; G06N 3/08
See application file for complete search history.

(56) References Cited

U.S. PATENT DOCUMENTS

| | | | |
|---|---|---|---|
| 2009/0097729 A1* | 4/2009 | Venkatachalam | ........ G06K 9/00 382/132 |
| 2019/0012802 A1 | 1/2019 | Liu et al. | |

(Continued)

FOREIGN PATENT DOCUMENTS

| | | |
|---|---|---|
| EP | 0 437 280 A2 | 7/1991 |
| EP | 3 825 957 A1 | 5/2021 |

(Continued)

OTHER PUBLICATIONS

Notice of Allowance dated Mar. 17, 2022 issued in corresponding Korean Application No. 10-2021-0123908; 14 pages.

(Continued)

*Primary Examiner* — Courtney D Thomas
(74) *Attorney, Agent, or Firm* — Maier & Maier, PLLC

(57) ABSTRACT

A non-destructive inspection apparatus is provided. The non-destructive inspection apparatus includes at least one memory configured to store commands for performing predetermined operations, and at least one processor operatively coupled to the at least one memory and configured to execute the commands. The at least one processor is configured to obtain information on a transmission amount of an X-ray by emitting the X-ray to a part of a bicycle, generate a gray scale image based on the information on the transmission, measure an amount of change in a gray value from one end to the other end of the part of the bicycle represented in the gray scale image along an extending direction of the part, and detect an area in which the amount of change in the gray value is equal to or greater than a threshold, as an abnormal area.

15 Claims, 15 Drawing Sheets

(56) References Cited

U.S. PATENT DOCUMENTS

| | | | | |
|---|---|---|---|---|
| 2020/0234425 A1* | 7/2020 | Furuichi | ............... | G01N 23/083 |
| 2021/0096089 A1 | 4/2021 | Shimizu | | |
| 2021/0142467 A1* | 5/2021 | Burkhardt | ............... | G06N 20/00 |

FOREIGN PATENT DOCUMENTS

| | | | |
|---|---|---|---|
| JP | 2004-294287 | A | 10/2004 |
| JP | 2009-544982 | A | 12/2009 |
| KR | 10-2157233 | B1 | 9/2020 |
| KR | 10-2021-0024767 | A | 3/2021 |

OTHER PUBLICATIONS

Office Action dated Dec. 20, 2021 issued in corresponding Korean Application No. 10-2021-0123908; 7 pages.
Korean Patent No. 10-2390004 issued Apr. 20, 2022 in corresponding Korean Application No. 10-2021-0123908; (with English translation of granted claims); 33 pages.
YouTube video ("I took a non-destructive inspection (X-ray) of Eunbi's repaired carbon bike!!!!") (captured photo) URL: https://www.youtube.com/watch?v=G7zJggTHkXI (Feb. 24, 2021); 1 page.

* cited by examiner

1  #2  #3  #4  #5

FIG.8A
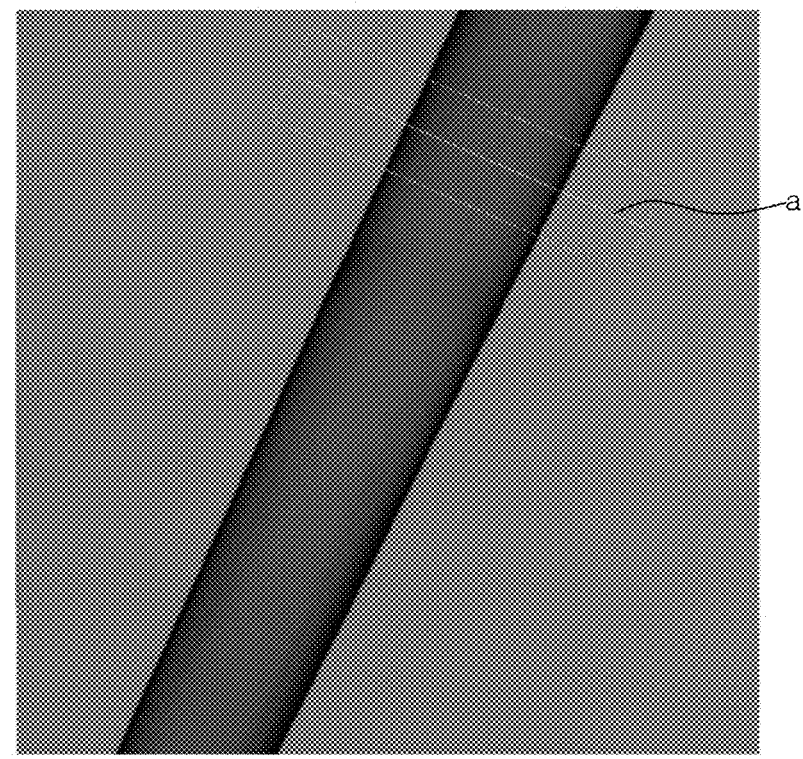
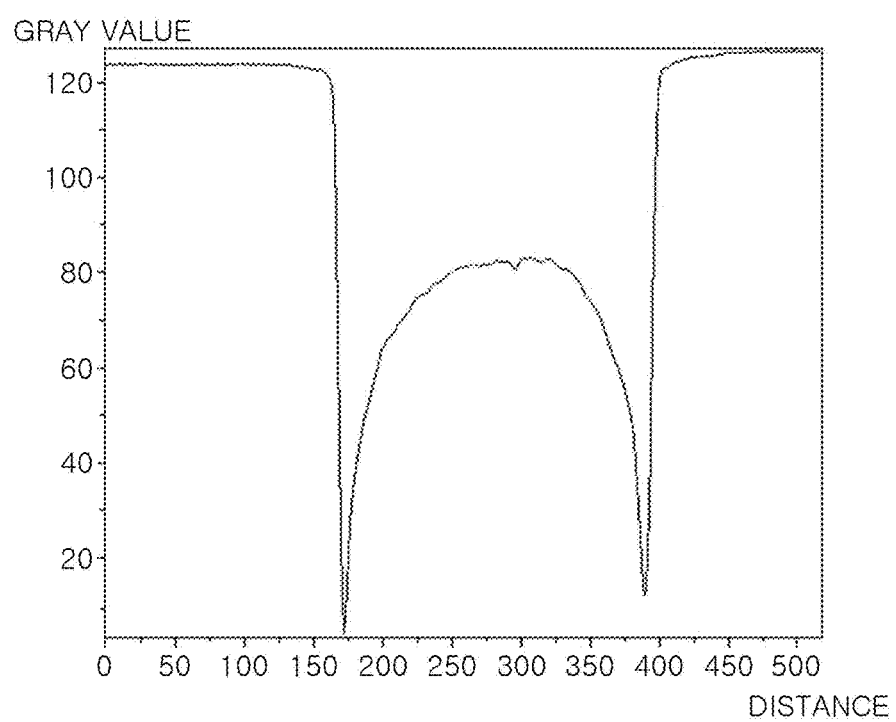

FIG.8B
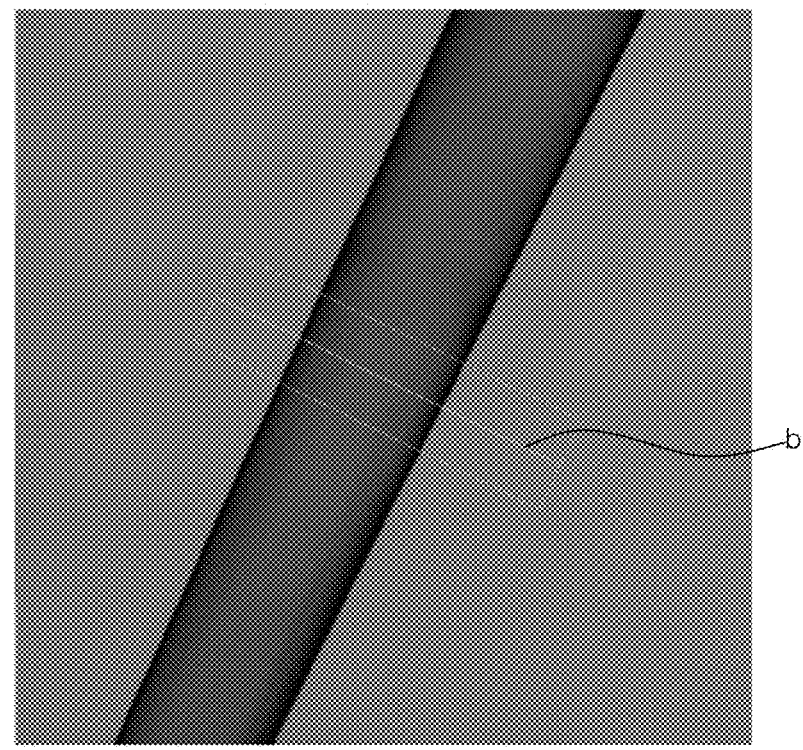
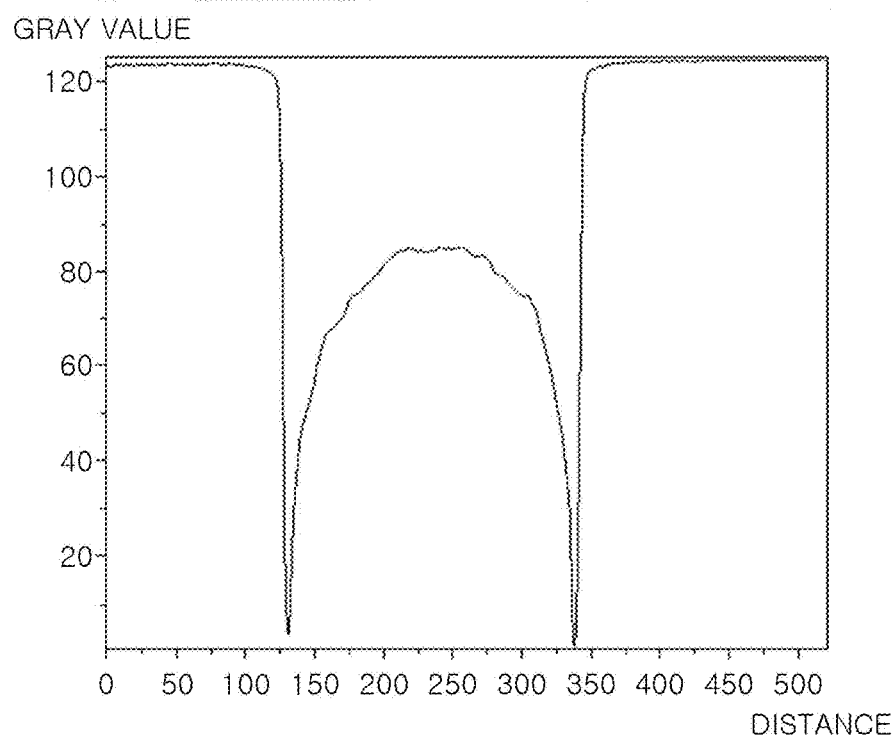

FIG. 8C
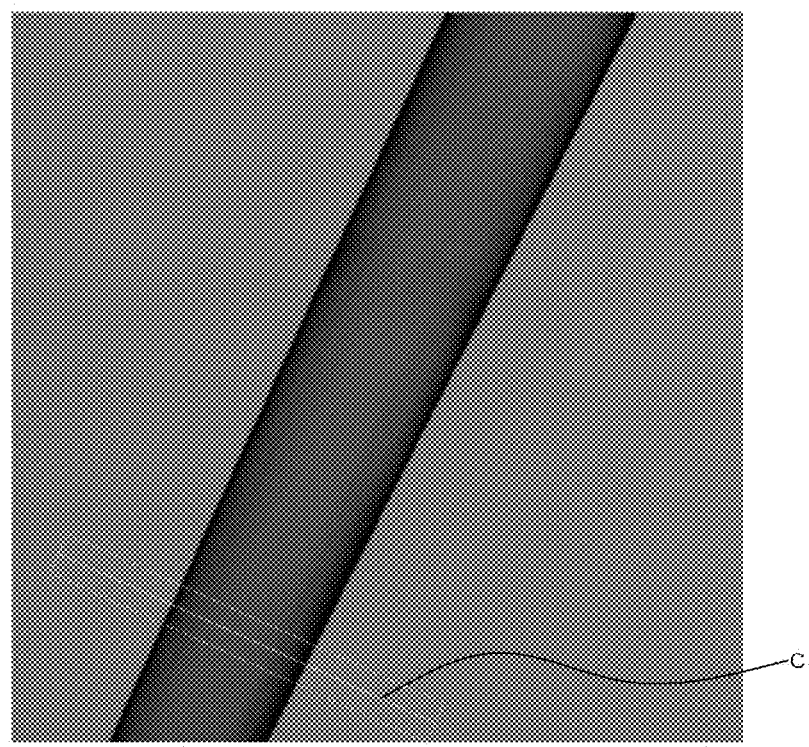
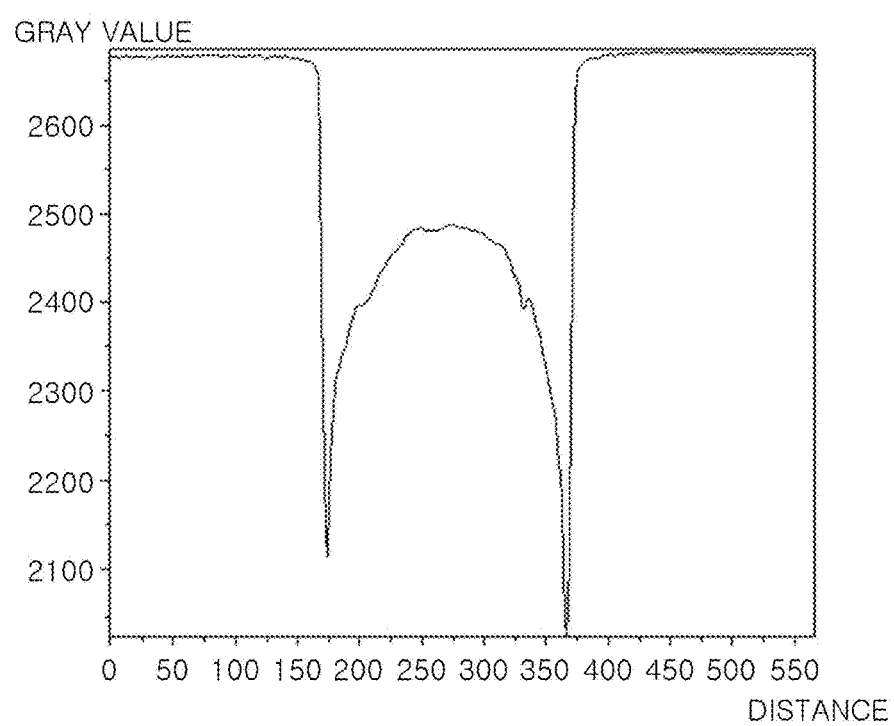

FIG. 9A
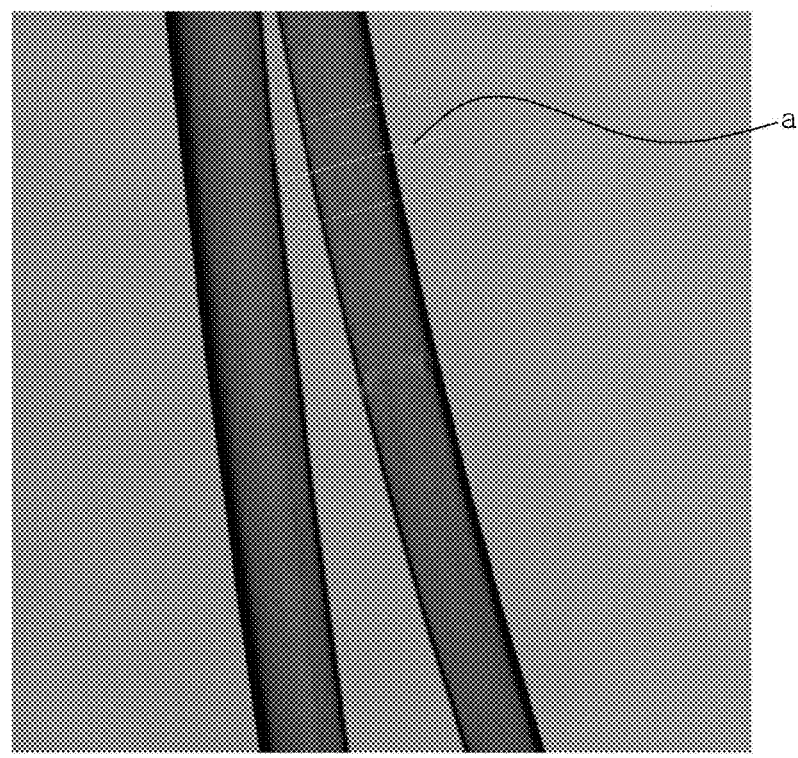
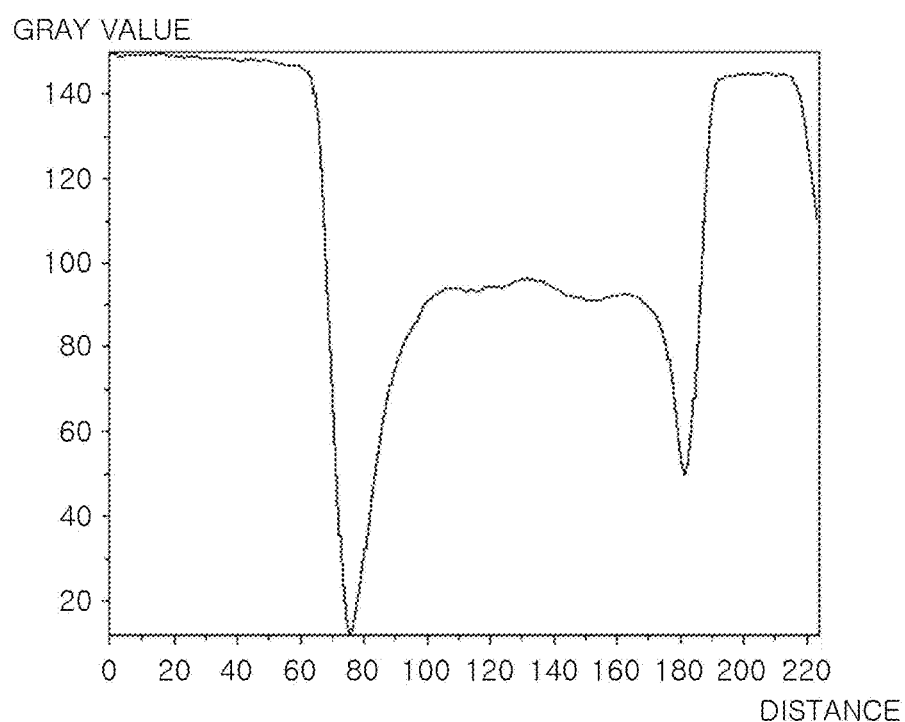

FIG.9B
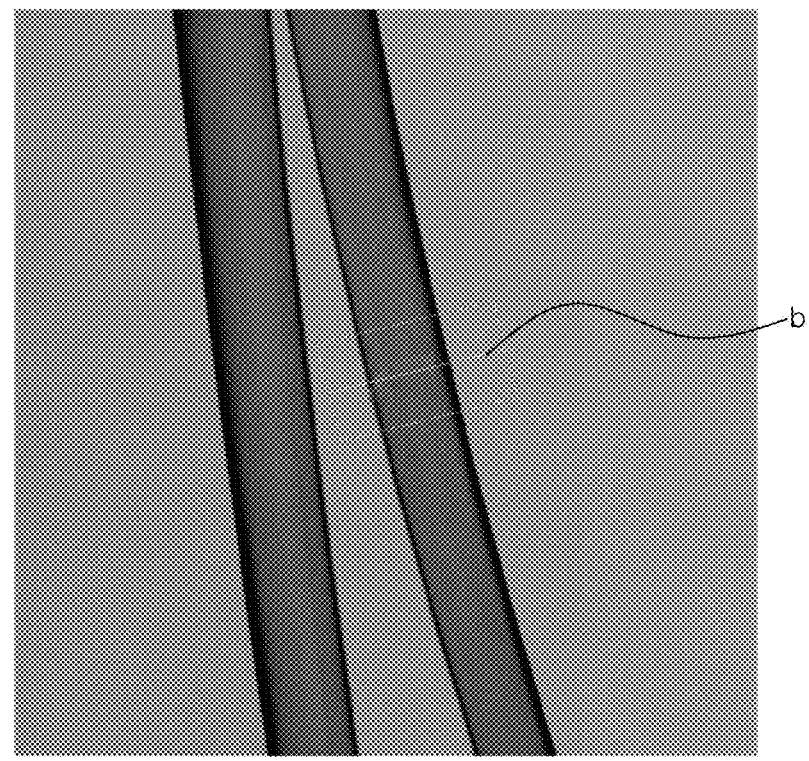
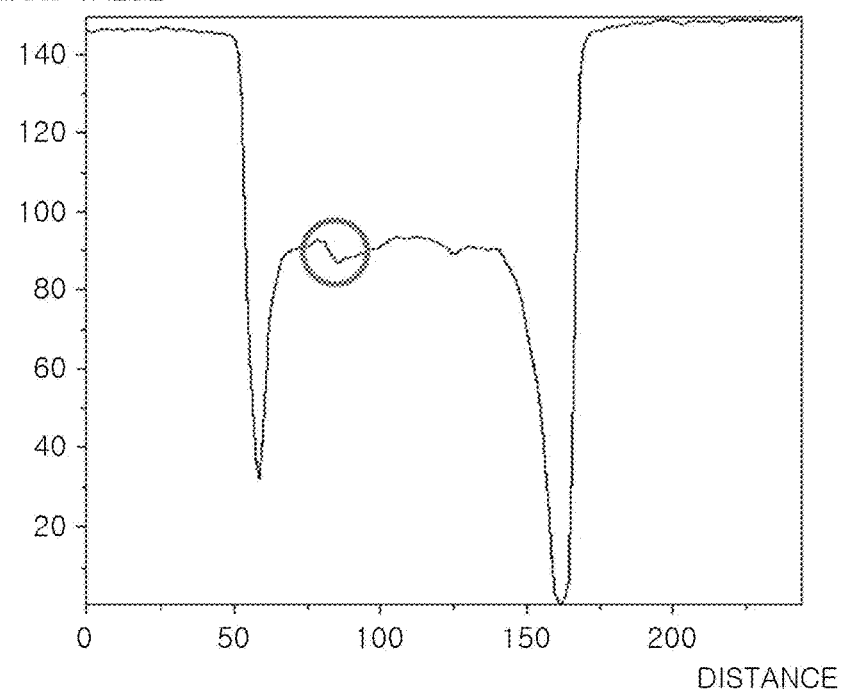

FIG.9C
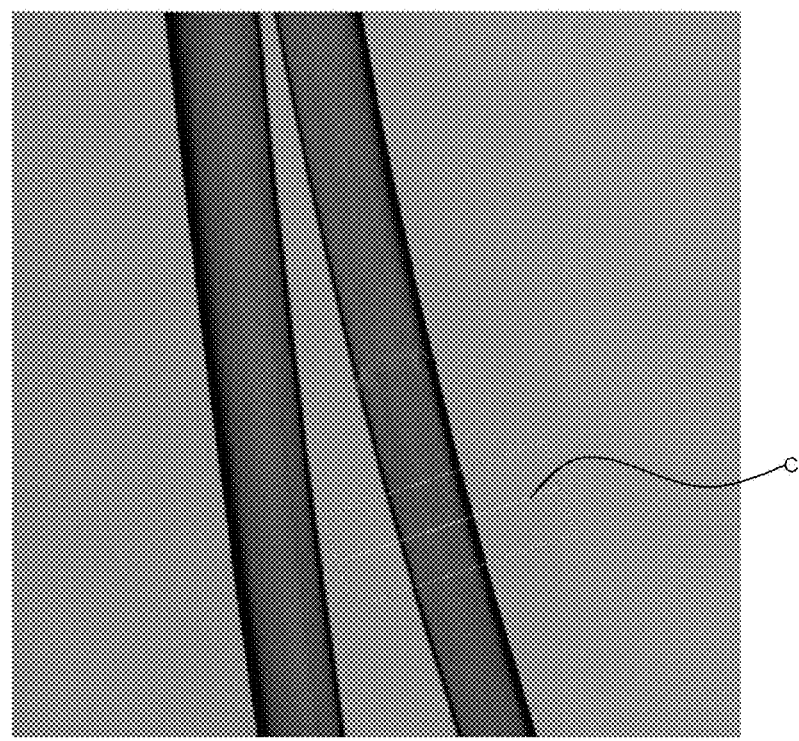
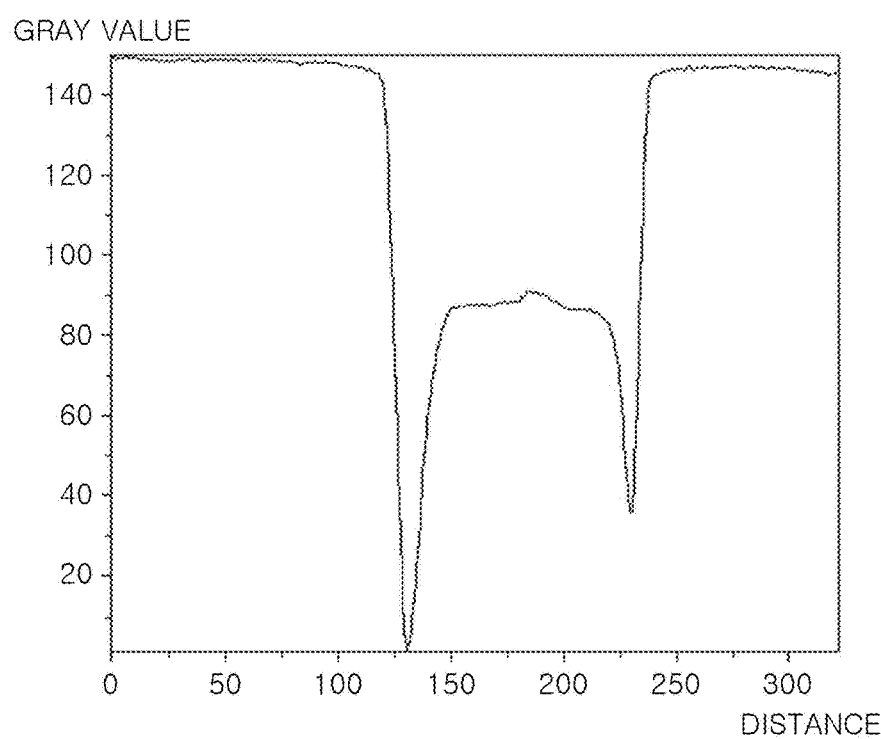

APPARATUS, METHOD, COMPUTER-READABLE STORAGE MEDIUM FOR NON-DESTRUCTIVE INSPECTION OF BICYCLE BASED ON ANALYZING AMOUNT OF SCALE VALUE CHANGE

CROSS-REFERENCE TO RELATED APPLICATION

This application claims priority to Korean Patent Application No. 10-2021-0123908, filed on Sep. 16, 2021. The entire contents of the application on which the priority is based are incorporated herein by reference.

TECHNICAL FIELD

The present disclosure relates to a technique for performing non-destructive inspection of a part of a bicycle based on a scale change analysis of a transmission amount of X-ray.

BACKGROUND

A bicycle is a means of transportation that a person steps on a pedal to move, and as the bicycle is made of a light and strong material, the efficiency and stability of movement increase. Accordingly, recently, a bicycle made of a carbon composite material, which is light in weight and relatively strong, has been developed and manufactured.

Meanwhile, among parts of a bicycle, there are parts made so thin that a thickness of the carbon composite material is less than 1 mm, and thus, pores may occur inside the carbon composite material during the manufacturing process. Accordingly, the weight or impact of a user may cause damage to the part during use, and cracks easily occur in the part.

Abnormal portions such as the pores or cracks have a great influence on stability of the bicycle. For example, a defect in the abnormal portion may lead to a serious accident due to damage while the bicycle is running, and the bicycle having the abnormal portion may be traded as a normal bicycle in the second-hand market. Accordingly, a buyer who buys the bicycle without being aware of these problems may have accidents or damage.

However, the abnormal portion of the carbon composite material is very fine, so it is difficult to identify the abnormal without an expert. Further, it is not possible to check the inside thereof without disassembling and inspecting the joint portion of the bicycle, so that the inspection process also has a problem in that required time and cost are considerable.

RELATED ART

Korean Patent No. 10-2157233

SUMMARY

In view of the above, embodiments of the present disclosure provide a technique for automatically detecting an abnormal portion of a bicycle through non-destructive inspection.

In particular, in order to automatically and accurately detect the abnormal portion, a technique for acquiring information on an analysis target from the bicycle for easy analysis and a technique for analyzing the meaning of the information by processing the acquired information are required. To this end, the embodiments of the present disclosure provide a pre-processing information acquisition process of generating an image suitable for non-destructive inspection of carbon, and a technology for detecting an abnormal portion of a part by processing the information obtained through the pre-processing information acquisition process.

Technical objects to be achieved by the present disclosure are not limited to those described above, and other technical objects not mentioned above may also be clearly understood from the descriptions given below by those skilled in the art to which the present disclosure belongs.

In accordance with an aspect of the present disclosure, there is provided a non-destructive inspection apparatus including: at least one memory configured to store commands for performing predetermined operations; and at least one processor operatively coupled to the at least one memory and configured to execute the commands. The at least one processor is configured to: obtain information on a transmission amount of an X-ray by emitting the X-ray to a part of a bicycle, generate a gray scale image based on the information on the transmission, measure an amount of change in a gray value from one end to the other end of the part of the bicycle represented in the gray scale image along an extending direction of the part, and detect an area in which the amount of change in the gray value is equal to or greater than a threshold, as an abnormal area.

Further, the X-ray may be emitted with a voltage in a range from 60 kV to 70 kV, a current in a range from 11.0 mA to 12.0 mA, and a focal point (FOC) in a range from 0.4 mm to 1.0 mm so as to obtain the gray scale of the part of the bicycle formed of carbon.

Further, in generating the gray scale image, the processor may be further configured to rescale an intensity of the transmission amount of the X-ray into an arbitrary unit intensity (a.u. intensity) between a minimum value of 0 and a maximum value of 3500, and select one template of a first template, a second template, a third template, a fourth template, and a fifth template depending on the part of the bicycle. When the first template is selected, only portions of the part having rescaled intensities of the transmission amount of the X-ray ranging from 2216 to 2500 may be converted into the gray scale. When the second template is selected, only portions of the part having rescaled intensities of the transmission amount of the X-ray ranging from 2108 to 3294 may be converted into the gray scale. When the third template is selected, only portions of the part having rescaled intensities of the transmission amount of the X-ray ranging from 1893 to 2878 may be converted into the gray scale. When the fourth template is selected, only portions of the part having rescaled intensities of the transmission amount of the X-ray ranging from 1257 to 2878 may be converted into the gray scale. Further, when the fifth template is selected, only portions of the part having rescaled intensities of the transmission amount of the X-ray ranging from 31 to 2410 may be converted into the gray scale.

Further, in measuring the amount of change in the gray value, the processor may be further configured to generate two-dimensional graph information in which the amount of change in the gray value is measured with an x-axis representing a movement distance of one point from the one end to the other end along the extending direction of the part and a y-axis representing the gray value of the gray scale measured when the one point is controlled to move on the x-axis.

Further, in detecting the abnormal area, when an amount of change in the y-axis within a predetermined range of the x-axis is equal to or greater than a preset threshold, the processor may be further configured to detect, as the abnormal area, a portion corresponding to an x-axis length at which the amount of change in the y-axis that is equal to or greater than the preset threshold is generated.

Further, in measuring the amount of change in the gray value, the processor may be further configured to generate a three-dimensional graph information in which the amount of change in the gray value is measured with a Z-axis representing a length of a cutting line cutting the part of the bicycle at the one end, an x-axis representing a movement distance of the cutting line from the one end to the other end along the extending direction of the part, and a y-axis representing the gray value of the gray scale measured while the cutting line is controlled to move on the x-axis.

Further, in detecting the abnormal area, when an amount of change in the y-axis within a predetermined range of the x-axis is equal to or greater than a preset threshold, the processor may be further configured to detect, as the abnormal area, a portion corresponding to an x-axis length at which the amount of change in the y-axis that is equal to or greater than the preset threshold is generated.

Further, in detecting the abnormal area, the processor may be further configured to detect, as the abnormal area, a three-dimensional area including the x-axis length and a z-axis length at which the amount of change in the y-axis is that is equal to or greater than the preset threshold is generated.

Further, in obtaining the information on the transmission amount, the processor may be further configured to specify the part of the bicycle by inputting an entire image of the bicycle to a first neural network model that is trained with an image data set for each part of the bicycle to which specification information for the corresponding part of the bicycle is mapped, and obtain information on the transmission amount of the X-ray for the specified part by adjusting a X-ray emission position to a position of the specified part. The specification information may include information specifying a type of the part and information on a voltage, a current, a focal length of the X-ray preset to perform non-destructive inspection on the part.

Further, the first neural network may be trained based on an image recognition algorithm, and the image data set for each part of the bicycle may include a data set in which a frame, a wheel, and a drivetrain are labeled in portions of the image.

Further, the processor may be further configured to determine a type of the abnormal area based on an image of the abnormal area after performing the detecting of the abnormal area.

Further, in determining the type of the abnormal area, the processor may be further configured to determine a class of the abnormal area by inputting the image of the abnormal area to a second neural network model that is trained with an abnormal image data set for each part of the bicycle, and calculate a price of the bicycle by reflecting depreciation information obtained based on the class of the abnormal area to specification information of the part including the abnormal area. The specification information may include information specifying the price of the part.

Further, the second neural network may be trained based on the image recognition algorithm, and the abnormal image data set for each part of the bicycle may include a data set in which breakage, repair, reinforcement, joint, and pores of the part are labeled in portions of the image.

In accordance with another aspect of the present disclosure, there is provided a non-destructive inspection method performed by a non-destructive inspection apparatus, the non-destructive inspection method including: acquiring information on a transmission amount of an X-ray by emitting the X-ray to a part of a bicycle; generating a gray scale image based on the information on the transmission amount; measuring an amount of change in a gray value from one end to the other end of a part of the bicycle represented in the gray scale image along an extending direction of the part; and detecting an area in which the amount of change in the gray value is equal to or greater than a threshold, as an abnormal area.

In accordance with still another aspect of the present disclosure, there is provided a non-transitory computer-readable storage medium including computer-executable instructions which cause, when executed by a processor, the processor to perform a non-destructive inspection method performed by a non-destructive inspection apparatus, the non-destructive inspection method including: acquiring information on a transmission amount of an X-ray by emitting the X-ray to a part of a bicycle; generating a gray scale image based on the information on the transmission amount; measuring an amount of change in a gray value from one end to the other end of a part of the bicycle represented in the gray scale image along an extending direction of the part; and detecting an area in which the amount of change in the gray value is equal to or greater than a threshold, as an abnormal area.

According to the aspects of the present disclosure, it is possible to simply detect an abnormal portion of the part without disassembling the bicycle, and it is possible to determine the type of the abnormal portion. Accordingly, it is possible to improve the inspection accuracy while effectively shortening the inspection process during manufacturing of the bicycle.

In addition, by allowing a certified institution to use the technique of the present disclosure, it becomes possible to certify the quality of bicycles in the second-hand market, thereby establishing a healthy trading culture and ensuring the safety of bicycle users.

The technical effects of the present disclosure are not limited to the technical effects described above, and other technical effects not mentioned herein may be understood to those skilled in the art to which the present disclosure belongs from the description below.

BRIEF DESCRIPTION OF THE DRAWINGS

FIG. 8A is an exemplary diagram for explaining an operation of detecting a part in a normal state according to one embodiment.

FIG. 8B is an exemplary diagram for explaining an operation of detecting a part in a normal state according to one embodiment.

FIG. 8C is an exemplary diagram for explaining an operation of detecting a part in a normal state according to one embodiment.

FIG. 9A is an exemplary diagram for explaining an operation of detecting a part including an abnormal area according to one embodiment.

FIG. 9B is an exemplary diagram for explaining an operation of detecting a part including an abnormal area according to one embodiment.

FIG. 9C is an exemplary diagram for explaining an operation of detecting a part including an abnormal area according to one embodiment.

DETAILED DESCRIPTION

Hereinafter, various embodiments of the present disclosure will be described with reference to the accompanying drawings. However, it should be understood that the specific embodiments are not intended to limit the gist of the present disclosure to the specific embodiments; rather, it should be understood that the specific embodiments include all of the modifications, equivalents, and/or alternatives of the embodiments of the present disclosure. Regarding the description of the drawings, the same or similar constituting elements are given the same or similar reference symbol numbers.

Figure 1:
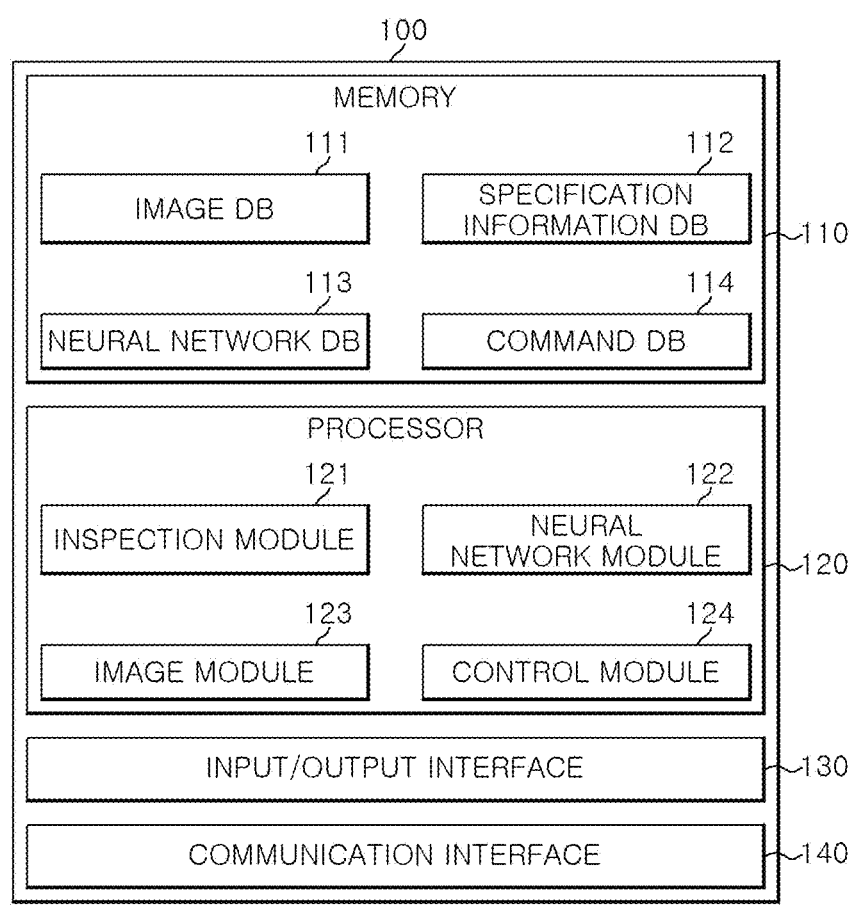
FIG. 1 is a functional block diagram of a non-destructive inspection apparatus according to one embodiment.

FIG. 1 is a functional block diagram of a non-destructive inspection apparatus 100 according to one embodiment.

Referring to FIG. 1, the non-destructive inspection apparatus 100 according to one embodiment may include a memory 110, a processor 120, an input/output interface 130, and a communication interface 140.

The memory 110 may include an image database (DB) 111, a specification information DB 112, a neural network DB 113, and a command DB 114.

The image DB 111 may store data for an entire image of a bicycle, an image of a part of the bicycle, an X-ray photographed image of the bicycle, and an image having a specified abnormal area of the X-ray photographed images of the bicycle. The image stored in the image DB 111 may be used for the training of a first neural network and a second neural network, which will be described below.

The specification information DB 112 may store detailed information of the part of the bicycle. For example, detailed information of the part includes a material, a use, a manufacturer, a production year, a brand of each part, a category, a year, an operation method, a color, a substance, a model name, a size, a minimum recommended key, a maximum recommended key, a geometry, an amount of carbon emitted at the time of manufacturing, a price, a voltage, a current, and a focal length of an X-ray that should be set to perform non-destructive inspection on the part, and template information that should be set to convert from X-ray transmission amount information obtained for the part to a gray scale.

The neural network DB 113 may store the trained neural network. For example, the neural network DB 113 may include a first neural network model that is trained with an image data set for each part of the bicycle to which specification information for the corresponding part of the bicycle is mapped. When a predetermined bicycle image is input to the first neural network model, a class (for example, frame, wheel, drivetrain, or the like) of the part included in the bicycle image is specified and the specification information of each part is output from the first neural network. For example, the neural network DB 113 may include a second neural network model that is trained with the abnormal image data set for each part of the bicycle, and when a predetermined abnormal area image is input to the second neural network model, a class (for example, breakage, repair, reinforcement, joint, pores, or the like) of the abnormal area is specified by the second neural network model.

The command DB 114 may store commands for performing an operation of the processor 120. For example, the command DB 114 may store computer code for performing operations corresponding to operations of the processor 120 to be described below.

The processor 120 may control the overall operation of the non-destructive inspection apparatus 100. The processor 120 may include an inspection module 121, a neural network module 122, an image module 123, and a control module 124. The processor 120 may execute the commands stored in the memory 110 to drive the inspection module 121, the neural network module 122, the image module 123, and the control module 124.

The inspection module 121 may be interlocked with a non-destructive imaging device (that is, X-RAY CT SCANNER) that performs imaging of a product using the X-ray, and may control the non-destructive imaging device. For example, the inspection module 121 may control the non-destructive imaging device to emit the X-ray to a part of the bicycle, and obtain information on an amount of the X-rays transmitted through the parts of the bicycle. The non-destructive inspection apparatus 100 may be connected to the non-destructive imaging device by wire or wireless.

The neural network module 122 may train and control the first neural network and the second neural network according to one embodiment.

Figure 2:
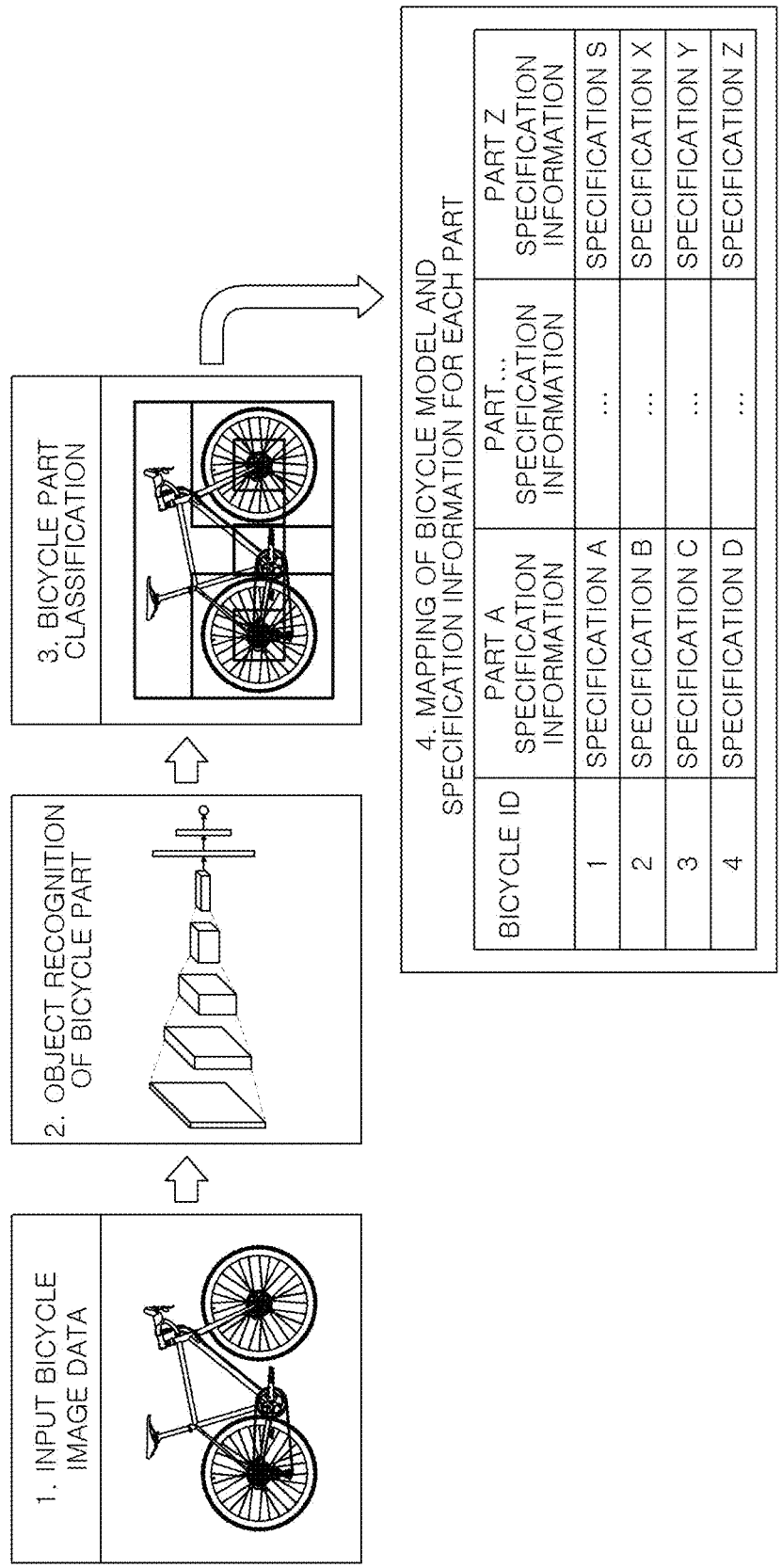
FIG. 2 is an exemplary diagram of a first neural network for classifying parts of a bicycle included in an overall image of a bicycle according to one embodiment.

FIG. 2 is an exemplary diagram of a first neural network for classifying parts of the bicycle included in the overall image of the bicycle according to one embodiment.

Referring to FIG. 2, the neural network module 122 may train the first neural network by using an image recognition algorithm with training images in each of which the position of each part constituting the bicycle is specified as a bounding box in the overall image of the bicycle and the class specifying the part is labeled. With the trained first neural network, when the bicycle image is input to the first neural network, the first neural network may extract feature values of the input image through a convolution operation, specify the positions of the parts of the bicycle included in the input image based on the extracted feature values, and output specification information mapped to the specified parts.

For example, the first neural network may specify and classify individual parts (for example, frame, crank, front derailleur, rear derailleur, wheel, lever, or the like) from the entire image of the bicycle, and may group a set (for example, frameset, drivetrain, wheelset, component) of individual parts which are operated in conjunction with each other. The neural network module 122 may store information on parts included in the input bicycle image in the form of a set based on the classified individual parts and sets of individual parts. For example, the neural network module 122 may group and specify the information of the parts included in the input bicycle images in the form of a set (fork, frame) of elements corresponding to the frameset, a set (front derailleur, rear derailleur, brake, lever, crank, cassette, chain) of elements corresponding to the group set, a set (tire, hub) of elements corresponding to the wheelset, and a set (stem, seat-post, handlebar, saddle) of elements corresponding to the component.

The neural network module 122 may search the specification information DB 112 for specification information corresponding to each specified part, and map and store the specification information corresponding to each specified part.

Figure 3:
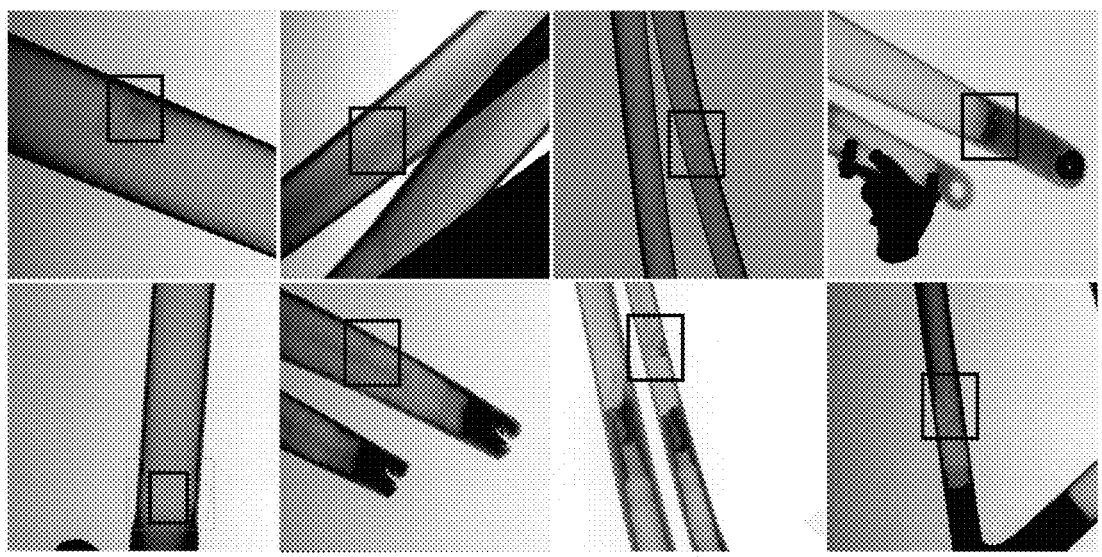
FIG. 3 is an exemplary diagram illustrating an image which is a result of detecting an abnormal area of a part according to one exemplary embodiment and is used for training a second neural network for determining a type of the abnormal area.

FIG. 3 is an exemplary diagram illustrating an image which is a result of detecting an abnormal area of a part according to one exemplary embodiment and is used for training a second neural network for determining a type of the abnormal area.

Referring to FIG. 3, the image used for the training of the second neural network may include an image directly labeled for training, or an image in which the abnormal area is automatically specified according to the embodiment (for example, steps S1010 to S1040 in FIG. 4) of the present disclosure and the type of the abnormal area is labeled. The class for the type of the abnormal area may include classes for pores, multi-pores, paint repair, resin excess, delamination, fiber damage, fiber mismatch, fiber repair, heat damage, foreign matter, joint damage, wrinkling, and disengagement.

Referring to FIG. 3, the neural network module 122 may train the second neural network by using a predetermined image recognition algorithm with the training images in each of which the abnormal area is specified as the bounding box and the class for the type of abnormal area is labeled. With the trained second neural network, when the image in which the abnormal area is specified is input to the second neural network, the second neural network may extract feature values of the input image through a convolution operation, and specify the position and type of the abnormal area included in the input image based on the extracted feature values.

The image module 123 may generate the gray scale image of the photographed bicycle part based on the information on the transmission amount obtained from the non-destructive imaging device.

The control module 124 may analyze the generated gray scale image to determine whether the abnormal area is included in the photographed part, and may specify the type of the determined abnormal area. The control module 124 may determine a repair method based on the type of the abnormal area or calculate the price of the corresponding part.

Operations performed by the inspection module 121, the neural network module 122, the image module 123, and the control module 124 described above may be understood as operations performed by the processor 120.

The input/output interface 130 may include a hardware interface or a software interface that allows a manager who controls the non-destructive inspection apparatus 100 to input specific information or outputs specific information to the manager.

The communication interface 140 enables the non-destructive inspection apparatus 100 to transmit and receive information to and from an external device (for example, non-destructive imaging device) through a communication network. To this end, the communication interface 140 may include a wireless communication module or a wired communication module.

The non-destructive inspection apparatus 100 may be implemented as various types of apparatuses capable of performing an operation through the processor 120 and transmitting/receiving information through a network. For example, the non-destructive inspection apparatus 100 may include a portable communication device, a smart phone, a computer device, a portable multimedia device, a notebook computer, a tablet PC, or the like.

Hereinafter, an embodiment of an operation performed by the non-destructive inspection apparatus 100 through the above-described configuration will be described along with FIGS. 4 to 11.

Figure 4:
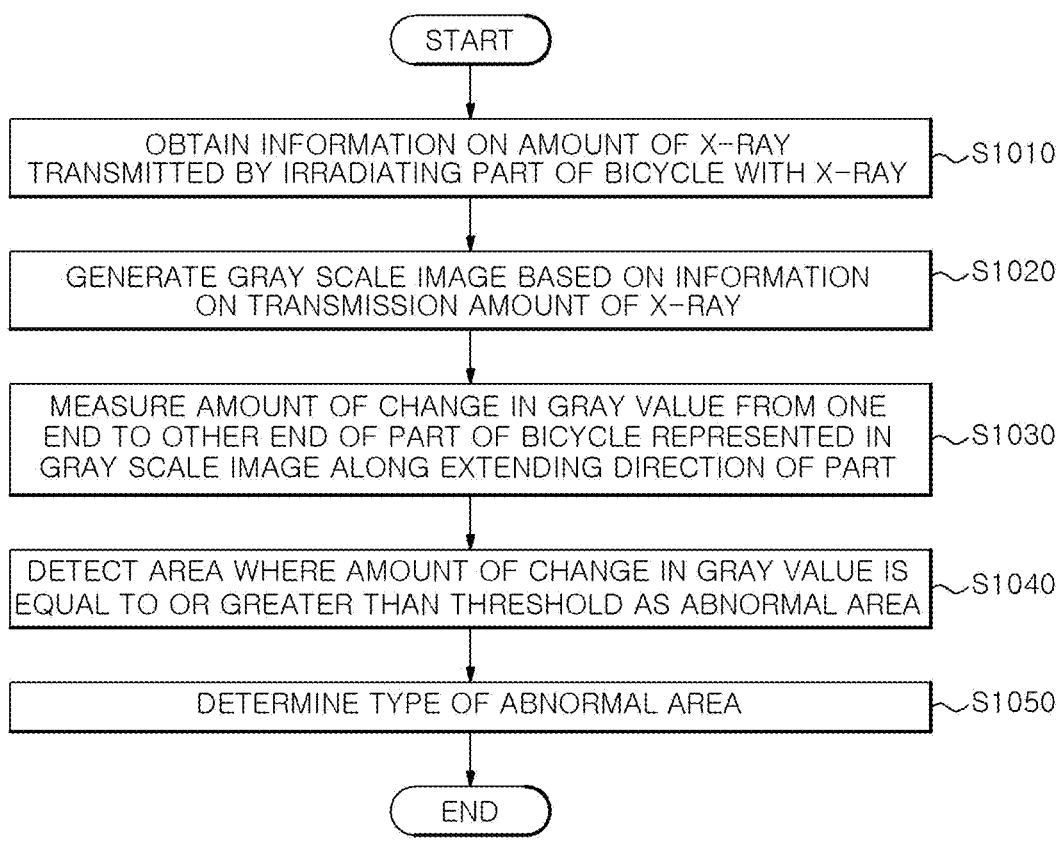
FIG. 4 is a flowchart of an operation in which the non-destructive inspection apparatus performs a non-destructive inspection method according to one embodiment.

FIG. 4 is a flowchart of an operation in which the non-destructive inspection apparatus 100 performs a non-destructive inspection method according to one embodiment.

Referring to FIG. 4, the inspection module 121 may control the non-destructive imaging device to emit X-rays to the part of the bicycle, and obtain information on the amount of X-rays transmitted through the part of the bicycle (step S1010).

The inspection module 121 performs an X-ray control for each part of the bicycle so that the control module 124 or the neural network module 122 detects the abnormal portion with high accuracy and generates information that is easy to determine the abnormal area. This is because, as illustrated in FIGS. 5A to 5C, information on the abnormal area may be included or lost depending on how the properties of the X-rays are controlled.

Figure 5A:
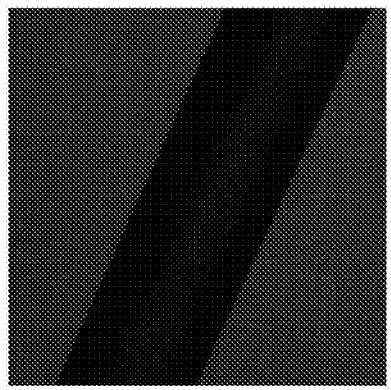
FIG. 5A is an exemplary diagram of a gray scale image generated from information obtained by changing properties of X-rays for the same object.
Figure 5B:
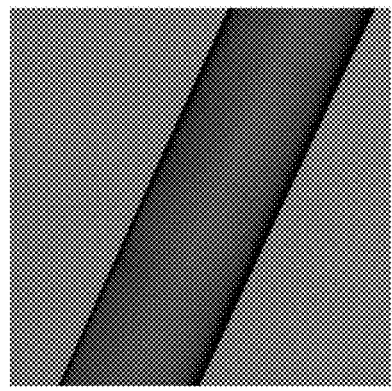
FIG. 5B is an exemplary diagram of a gray scale image generated from information obtained by changing properties of X-rays for the same object.
Figure 5C:
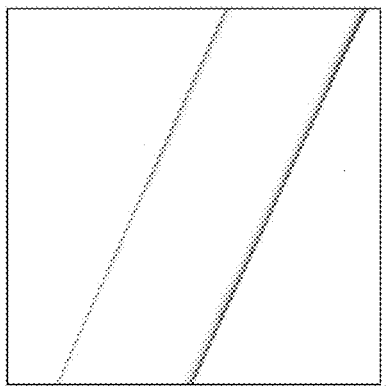
FIG. 5C is an exemplary diagram of a gray scale image generated from information obtained by changing properties of X-rays for the same object.

FIGS. 5A to 5C are exemplary diagrams of gray scale images respectively generated from information obtained by changing the properties of the X-rays for the same object.

Referring to FIGS. 5A to 5C, when the transmission amount of X-rays is too low, an image such as FIG. 5A is generated, and when the transmission amount of the X-rays is too high, an image such FIG. 5C is generated. Accordingly, it is important to obtain an image such as FIG. 5B by appropriately controlling the properties of the X-rays depending on each part.

The inspection module 121 may adjust the properties of the X-rays for each part based on the characteristics of the corresponding part that is a target to be photographed. For example, when the inspection module 121 photographs the parts of the bicycle formed of carbon, the inspection module 121 may control the non-destructive imaging device to emit the X-rays so that a voltage in a range from 60 kV to 70 kV, a current in a range from 11.0 mA to 12.0 mA, and a focal point (FOC) in a range from 0.4 mm to 1.0 mm are set during the radiation of the X-rays.

Before the inspection module 121 performs the X-ray photographing operation, the neural network module 122 may photograph the entire image of the bicycle that is a non-destructive inspection target and input the photographed image to the first neural network model trained with the image data set for respective parts of the bicycle to which pieces of the specification information for the respective parts of the bicycle are mapped. Then, the neural network module 122 may specify the positions and types of the parts of the bicycle to be inspected. The inspection module 121 may search the specified specification information for each part in the specification information DB 112. The specification information for each part may include information on the voltage, current, and focal length of X-rays that are preset to perform non-destructive inspection on each part. The inspection module 121 may control properties of X-rays based on the information stored in the specification information by adjusting a X-ray emission position to a position of a specified part, and thus, obtain the information of the transmission amount suitable for analysis for each part.

Next, the image module 123 may generate the gray scale image based on the acquired information of the transmission amount (step S1020).

The image module 123 determines which range of the acquired information on the transmission amount is converted into the gray scale to allow the control module 124 or the neural network module 122 to detect the abnormal portion with high accuracy, and creates an image that is easy to determine the abnormal area. This is because the information on the abnormal area may be included or lost depending on which range of the acquired information on the transmission amount is converted into the gray scale.

Figure 6:
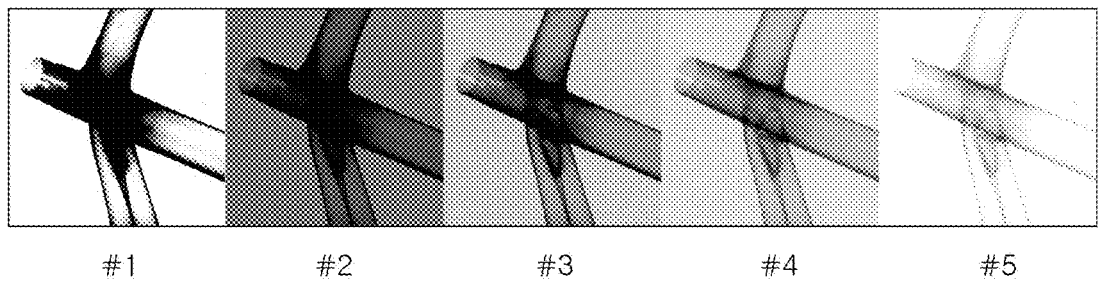
FIG. 6 is an exemplary diagram of the gray scale images in which a part of the bicycle is converted into the gray scale by changing an intensity of the transmission amount of X-rays.

FIG. 6 is an exemplary diagram of the gray scale images in which the part of the bicycle is converted into the gray scale by changing an intensity of the transmission amount of X-rays.

Referring to FIG. 6, the image module 123 may rescale an intensity of the transmission amount of the X-rays into an arbitrary unit intensity (a.u. intensity) between a minimum value of 0 and a maximum value of 3500, and select, depending on the part of the bicycle, one template of a first template, a second template, a third template, a fourth template, and a fifth template. When the first template is selected, only portions of the part having rescaled intensities of the transmission amount of the X-ray ranging from 2216 to 2500 are converted into the gray scale. When the second template is selected, only portions of the part having rescaled intensities of the transmission amount of the X-ray ranging from 2108 to 3294 are converted into the gray scale. When the third template is selected, only portions of the part having rescaled intensities of the transmission amount of the X-ray ranging from 1893 to 2878 are converted into the gray scale. When the fourth template is selected, only portions of the part having rescaled intensities of the transmission amount of the X-ray ranging from 1257 to 2878 are converted into the gray scale. When the fifth template is selected, only portions of the part having rescaled intensities of the transmission amount of the X-ray ranging from 31 to 2410 are converted into the gray scale.

For example, since a dark gray scale image with high contrast is generated by the conversion using the first template, the first template may be stored in the specification information such that the first template is used for inspection of a part of which a cross section or a side surface such as a thickness or a shape of an outline is needed to be checked.

Further, since a dark gray scale image with little contrast is generated by the conversion using the second template, the second template may be stored in the specification information such that the second template is used for inspection of a part of which the state of the surface is needed to be carefully checked.

Further, since a gray scale image having the contrast and brightness in a balanced way is generated by the conversion using the third template, the third template may be stored in the specification information such that the third template is used for inspection of a part of which all elements of all surfaces and lines are needed to be inspected.

Further, since a bright gray scale image with a relatively large contrast is generated by the conversion using the fourth template, the fourth template may be stored in the specification information such that the fourth template is used for inspection of a part having a relatively large thickness or low X-ray transmission due to an overlapping structure.

Further, since a bright gray scale image with little contrast is generated by the conversion using the fifth template, the fifth template may be stored in the specification information such that the fifth template is used for inspection of a part manufactured by mixing metal elements and three or more overlapped thick parts.

Next, the control module 124 may measure an amount of change in the gray value from one end to the other end of the part of the bicycle represented in the gray scale image along the extending direction of the part (step S1030), and detect an area where the amount of change in the gray value is equal to or greater than a threshold as the abnormal area (step S1040).

Figure 7:
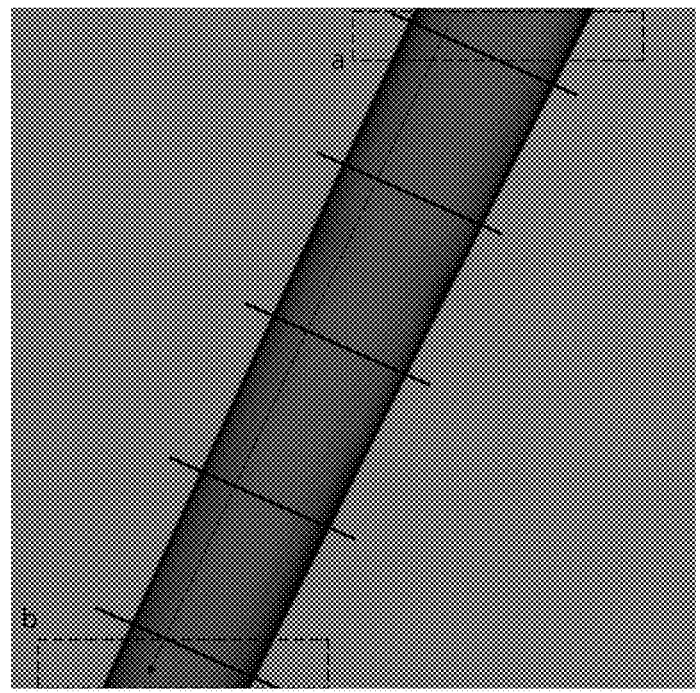
FIG. 7 is an exemplary diagram for explaining an operation of measuring the amount of change in the gray value according to one embodiment while controlling a cutting line located at one end of a part of a bicycle to move to the other end of the part of the bicycle along an extending direction of the part.

FIG. 7 is an exemplary diagram for explaining an operation of measuring the amount of change in the gray value according to one embodiment while controlling a cutting line located at one end 'a' of the part of the bicycle to move to the other end 'b' of the part of the bicycle along the extending direction of the part.

Referring to FIG. 7, the control module 124 may measure a value (gray value) of the gray scale along a cutting line orthogonal to the outer surface of the part recognized in the gray scale image.

FIGS. 8A to 8C are exemplary diagrams for explaining an operation of detecting the part in a normal state according to one embodiment. For the sake of convenience of understanding, FIGS. 8A to 8C show examples of measuring the values of the gray scale measured at each of the cutting lines of three portions a, b, and c spaced apart from each other.

Referring to each of FIGS. 8A to 8C, the control module 124 may measure the values of the gray scale along the cutting line orthogonal to the outer surface of the part recognized in the gray scale image. Referring to the graphs for the measurements at the three portions a, b, and c of FIGS. 8A to 8C, the value of the gray scale measured at the cutting line of each portion is not abruptly changed but is substantially maintained constant.

FIGS. 9A to 9C are exemplary diagrams for explaining an operation of measuring the part including the abnormal area according to one embodiment. For the sake of convenience of understanding, FIGS. 9A to 9C show examples of measuring the values of the gray scale measured at each of the cutting lines of the three portions a, b, and c spaced apart from each other.

Referring to FIGS. 9A to 9C, the control module 124 may measure the values of the gray scale along the cutting line orthogonal to the outer surface of the part recognized in the gray scale image. Referring to the graphs for the measurements at the three portions a, b, and c of FIGS. 9A to 9C, compared to the shape of the graph for the cutting line of the portion a or c, it was found that the value of the gray scale is abruptly changed in one section of the graph for the cutting line of the portion b.

Figure 10:
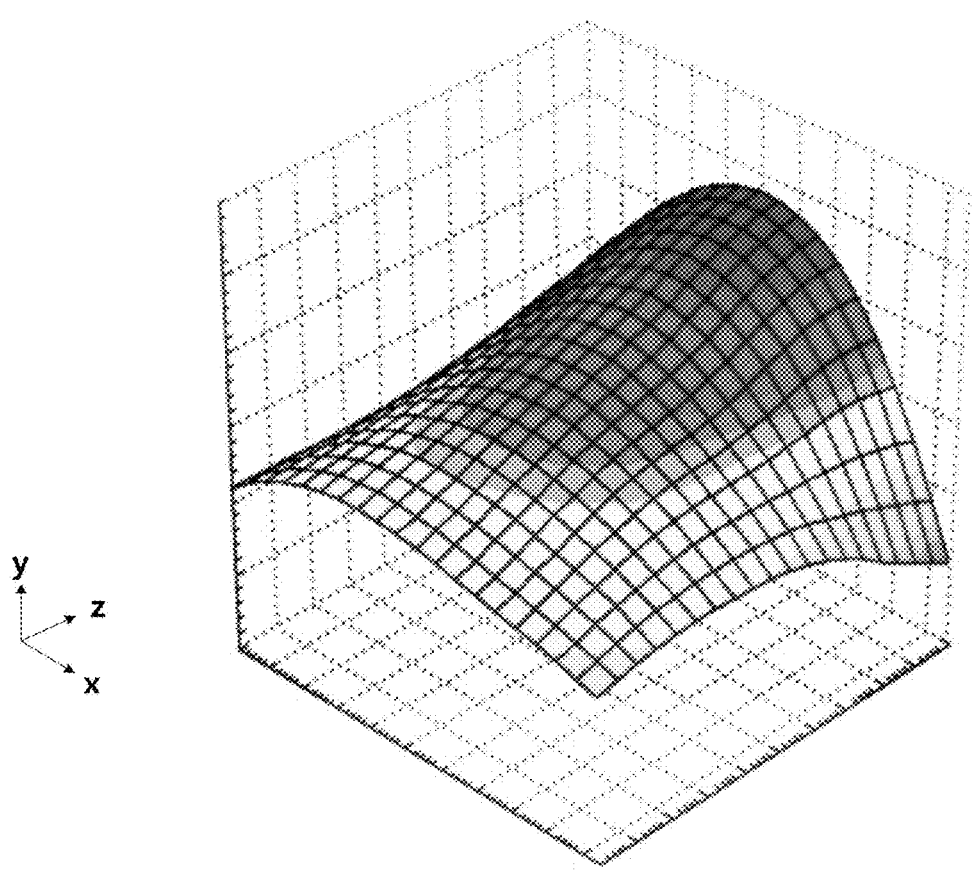
FIG. 10 is an exemplary diagram of a three-dimensional graph information generated based on the amount of change in the gray value measured according to one embodiment.

In one embodiment of the present invention, paying attention to the fact that one or more sections in which the value of the gray scale is abruptly changed are present in the abnormal area of the gray scale image photographed by the X-rays having suitable properties, the abnormal area may be detected based on the continuously measured amount of change in the gray value as illustrated in FIG. 10.

FIG. 10 is an exemplary diagram of a three-dimensional graph information generated based on the amount of change in the gray value measured according to one embodiment.

Referring to FIG. 10, the control module 124 may generate a three-dimensional graph information in which the amount of change in the gray value is measured with a Z-axis representing a length of the cutting line cutting the part at the one end of the part, an x-axis representing a movement distance of the cutting line from the one end to the other end along the extending direction of the part, and a y-axis representing a value of the gray scale measured while the cutting line moves on the x-axis. When there is at least one area where the amount of change in the y-axis within a predetermined range of the x-axis among the three-dimensional graph information is equal to or greater than a preset threshold, the control module 124 may detect, as the abnormal area, a portion corresponding to an x-axis length at which the amount of change in the y-axis that is equal to or greater than the preset threshold is generated. Moreover, the control module 124 may detect, as the abnormal area, a three-dimensional area including the x-axis length and a z-axis length at which the amount of change in the y-axis equal to or greater than the preset threshold is generated.

Figure 11:
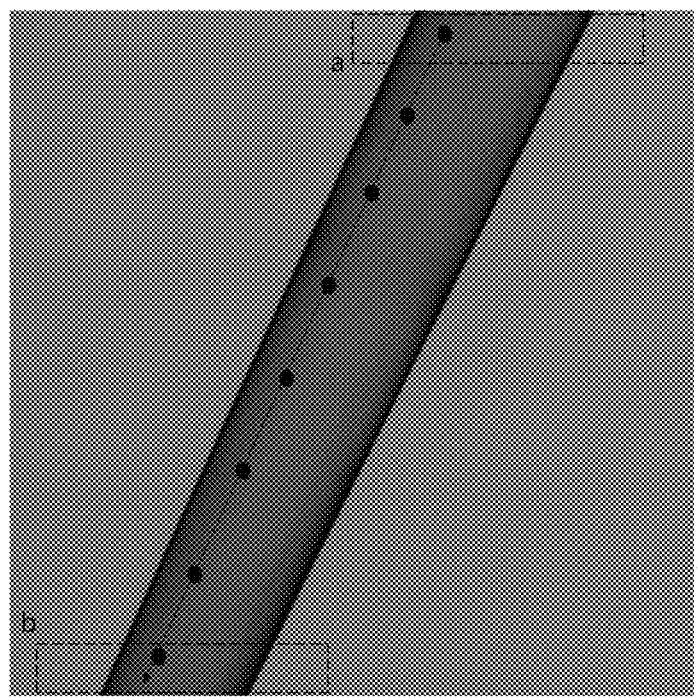
FIG. 11 is an exemplary diagram for explaining an operation of measuring the amount of change in gr value while controlling a point located at one end of the part of the bicycle to move to the other end of the part of the bicycle along the extending direction of the part, according to one embodiment.

FIG. 11 is an exemplary diagram for explaining an operation of measuring the amount of change in the gray value while controlling a point located at one end 'a' of the part of the bicycle to move to the other end 'b' of the part of the bicycle along the extending direction of the part, according to one embodiment.

Referring to FIG. 11, the control module 124 may measure the values of the gray scale along a direction parallel to the outer surface of the part recognized in the gray scale image. The control module 124 may generate two-dimensional graph information in which the amount of change in the gray value is measured with an x-axis representing a movement distance of one point from the one end to the other end along the extending direction of the part and a y-axis representing a value of the gray scale measured when the one point is controlled to move on the x-axis. When there is at least one point at which the amount of change in the y-axis within a predetermined range of the x-axis among the two-dimensional graph information is equal to or greater than a preset threshold, the control module 124 may detect, as the abnormal area, a portion corresponding to an x-axis length at which the amount of change in the y-axis that is equal to or greater than the preset threshold is generated.

Next, the control module 124 may determine the type of the abnormal area based on an image of the specified abnormal area (step S1050).

For example, the control module 124 may determine the class of the abnormal area by inputting the image of the detected abnormal area to the second neural network model that is trained with the abnormal image data set for each part of the bicycle. The control module 124 may calculate the price by reflecting depreciation information obtained based on the class of the abnormal area to the specification information of the part including the abnormal area. For example, by reflecting depreciation information (for example, a price drop of 10% when the class of the detected abnormal area is the pore, or a price drop of 15% when the class of the detected abnormal area is the joint) to an original price derived based on the specification information of the specified part, it is possible to recalculate the price according to the existence of the abnormal area. The control module 124 may search the specification information DB 112 to find a repair method according to the type of the abnormal area of the corresponding part, and output the repair method or the repair price of the abnormal area of the corresponding part.

According to the above-described embodiments, it is possible to simply detect an abnormal portion of the part without disassembling the bicycle, and it is possible to determine the type of the abnormal portion. Accordingly, it is possible to improve the inspection accuracy while effectively shortening the inspection process during manufacturing of the bicycle. In addition, by allowing a certified institution to use the technique of the present disclosure, it becomes possible to certify the quality of bicycles in the second-hand market, thereby establishing a healthy trading culture and ensuring the safety of bicycle users.

Various embodiments of the present disclosure and terms used therein are not intended to limit the technical characteristics disclosed in the present disclosure to the specific embodiments, which should be understood to include various modifications, equivalents, or substitutes of the corresponding embodiment. Regarding the description of the drawings, like reference numerals may be given to substantially like parts. A singular expression of a noun corresponding to an item may include one or more items unless relevant context explicitly dictates otherwise.

In the present disclosure, each of the phrases such as "A or B," "at least one of A and B," "at least one of A or B," "A, B, or C," "at least one of A, B, and C," and "at least one of A, B, or C" may include all possible combinations of the items listed together in the corresponding phrase. Terms such as "first" or "second" may be used simply to distinguish one constituting element from the other constituting element and do not limit the corresponding constituting elements in favor of another aspect (for example, importance or order). When a particular (for example, first) constituting element is said to be "coupled" or "connected" to another (for example, second) constituting element with or without the term "functionally" or "communicatively," it means that the particular constituting element may be linked to another constituting element directly (for example, in a wired manner), wirelessly, or through a third constituting element.

The term "module" used in the present disclosure may include a unit implemented using hardware, software, or firmware. For example, the term "module" may be used interchangeably with a term such as logic, logic block, component, or circuit. A module may be an integral component or a minimum unit of a component or a part thereof that performs one or more functions. For example, according to one embodiment, a module may be implemented in the form of application-specific integrated circuit (ASIC).

Various embodiments of the present disclosure may be implemented as software (for example, a program) including one or more instructions stored in a storage medium (for example, memory) readable by a device (for example, an electronic device). The storage medium may include a random access memory (RAM), a memory buffer, a hard drive, a database, an erasable programmable read-only memory (EPROM) an electrically erasable read-only memory (EEPROM), a read-only memory (ROM) and/or the like.

Further, the processor according to the embodiments of the present disclosure may call at least one instruction among one or more stored instructions from the storage medium and execute the instruction called. This operation enables a device to perform at least one function according to at least one instruction called. The one or more instructions may include code generated by a compiler or code executable by an interpreter. The processor may be a general-purpose processor, a field programmable gate array (FPGA), the ASIC, a digital signal processor (DSP) and/or the like.

A machine-readable storage medium may be provided in the form of a non-transitory storage medium. Here, the term "non-transitory" only indicates that the storage medium is a tangible device but does not include a signal (for example, electromagnetic waves). The term "non-transitory", therefore, does not distinguish a case in which data is stored in a storage medium semi-permanently from a case in which data is stored temporarily.

Methods according to various embodiments of the present disclosure may be provided by being included in a computer program product. The computer program product may be traded between sellers and buyers as a commodity. The computer program product may be distributed in the form of a machine-readable storage medium (for example, a CD-ROM) or directly online (for example, download or upload) through an application store (for example, Play Store) or between two user devices (for example, smartphones). In the case of online distribution, at least part of the computer program product may be at least stored temporarily or generated temporarily in a server of the manufacturer, a server of the application store, or a machine-readable storage medium such as a memory of a relay server.

According to various embodiments, each of the constituting elements (for example, a module or a program) may be composed of single or multiple entities. According to various embodiments, one or more constituting elements or operations may be omitted from among the corresponding constituting elements described above, or one or more other constituting elements or operations may be added. Alternatively or additionally, a plurality of constituting elements (for example, a module or a program) may be integrated into a single constituting element. In this case, the integrated constituting elements may perform one or more functions of each of the plurality of constituting elements in the same manner or in a similar manner as performed by the corresponding constituting element of the plurality of constituting elements before the integration. According to various embodiments, the operations executed by a module, a program, or another constituting element may be performed in a sequential, parallel, repetitive, or heuristic manner; or one or more operations may be performed in a different order or omitted, or one or more different operations may be added to the operations.

What is claimed is:

1. A non-destructive inspection apparatus comprising:
   at least one memory configured to store commands for performing predetermined operations; and
   at least one processor operatively coupled to the at least one memory and configured to execute the commands, wherein the at least one processor is configured to:
   obtain information on a transmission amount of an X-ray by emitting the X-ray to a part of a bicycle,
   generate a gray scale image based on the information on the transmission,
   measure an amount of change in a gray value from one end to the other end of the part of the bicycle represented in the gray scale image along an extending direction of the part, and
   detect an area in which the amount of change in the gray value is equal to or greater than a threshold, as an abnormal area,
   wherein, in obtaining the information on the transmission amount, the processor is further configured to:
   specify the part of the bicycle by inputting an entire image of the bicycle to a first neural network model that is trained with an image data set for each part of the bicycle to which specification information for the corresponding part of the bicycle is mapped; and
   obtain information on the transmission amount of the X-ray for the specified part by adjusting an X-ray emission position to a position of the specified part.

2. The non-destructive inspection apparatus of claim 1, wherein the X-ray is emitted with a voltage in a range from 60 kV to 70 kV, a current in a range from 11.0 mA to 12.0 mA, and a focal point (FOC) in a range from 0.4 mm to 1.0 mm so as to obtain the gray scale of the part of the bicycle formed of carbon.

3. The non-destructive inspection apparatus of claim 1, wherein, in generating the gray scale image, the processor is further configured to rescale an intensity of the transmission amount of the X-ray into an arbitrary unit intensity (a.u. intensity) between a minimum value of 0 and a maximum value of 3500, and select one template of a first template, a second template, a third template, a fourth template, and a fifth template depending on the part of the bicycle
   wherein when the first template is selected, only portions of the part having rescaled intensities of the transmission amount of the X-ray ranging from 2216 to 2500 are converted into the gray scale; when the second template is selected, only portions of the part having rescaled intensities of the transmission amount of the X-ray ranging from 2108 to 3294 are converted into the gray scale; when the third template is selected, only portions of the part having rescaled intensities of the transmission amount of the X-ray ranging from 1893 to 2878 are converted into the gray scale; when the fourth template is selected, only portions of the part having rescaled intensities of the transmission amount of the X-ray ranging from 1257 to 2878 are converted into the gray scale; and when the fifth template is selected, only portions of the part having rescaled intensities of the transmission amount of the X-ray ranging from 31 to 2410 are converted into the gray scale.

4. The non-destructive inspection apparatus of claim 1, wherein, in measuring the amount of change in the gray value, the processor is further configured to generate two-dimensional graph information in which the amount of change in the gray value is measured with an x-axis representing a movement distance of one point from the one end to the other end along the extending direction of the part and a y-axis representing the gray value of the gray scale measured when the one point is controlled to move on the x-axis.

5. The non-destructive inspection apparatus of claim 4, wherein, in detecting the abnormal area, when an amount of change in the y-axis within a predetermined range of the x-axis is equal to or greater than a preset threshold, the processor is further configured to detect, as the abnormal area, a portion corresponding to an x-axis length at which the amount of change in the y-axis that is equal to or greater than the preset threshold is generated.

6. The non-destructive inspection apparatus of claim 1, wherein, in measuring the amount of change in the gray value, the processor is further configured to generate a three-dimensional graph information in which the amount of change in the gray value is measured with a Z-axis representing a length of a cutting line cutting the part of the bicycle at the one end, an x-axis representing a movement distance of the cutting line from the one end to the other end along the extending direction of the part, and a y-axis representing the gray value of the gray scale measured while the cutting line is controlled to move on the x-axis.

7. The non-destructive inspection apparatus of claim 6, wherein, in detecting the abnormal area, when an amount of change in the y-axis within a predetermined range of the x-axis is equal to or greater than a preset threshold, the processor is further configured to detect, as the abnormal area, a portion corresponding to an x-axis length at which the amount of change in the y-axis that is equal to or greater than the preset threshold is generated.

8. The non-destructive inspection apparatus of claim 7, wherein, in detecting the abnormal area, the processor is further configured to detect, as the abnormal area, a three-dimensional area including the x-axis length and a z-axis length at which the amount of change in the y-axis is that is equal to or greater than the preset threshold is generated.

9. The non-destructive inspection apparatus of claim 1, wherein the specification information includes information specifying a type of the part and information on a voltage, a current, a focal length of the X-ray preset to perform non-destructive inspection on the part.

10. The non-destructive inspection apparatus of claim 9, wherein the first neural network is trained based on an image recognition algorithm, and
the image data set for each part of the bicycle includes a data set in which a frame, a wheel, and a drivetrain are labeled in portions of the image.

11. The non-destructive inspection apparatus of claim 1, wherein the processor is further configured to determine a type of the abnormal area based on an image of the abnormal area after performing the detecting of the abnormal area,
wherein, in determining the type of the abnormal area, the processor is further configured to determine a class of the abnormal area by inputting the image of the abnormal area to a second neural network model that is trained with an abnormal image data set for each part of the bicycle.

12. The non-destructive inspection apparatus of claim 11, wherein, in determining the type of the abnormal area,
the processor is further configured to
calculate a price of the bicycle by reflecting depreciation information obtained based on the class of the abnormal area to specification information of the part including the abnormal area, and
wherein the specification information includes information specifying the price of the part.

13. The non-destructive inspection apparatus of claim 12, wherein the second neural network is trained based on the image recognition algorithm, and
the abnormal image data set for each part of the bicycle includes a data set in which breakage, repair, reinforcement, joint, and pores of the part are labeled in portions of the image.

14. A non-destructive inspection method performed by a non-destructive inspection apparatus, the non-destructive inspection method comprising:
acquiring information on a transmission amount of an X-ray by emitting the X-ray to a part of a bicycle;
generating a gray scale image based on the information on the transmission amount;
measuring an amount of change in a gray value from one end to the other end of a part of the bicycle represented in the gray scale image along an extending direction of the part; and
detecting an area in which the amount of change in the gray value is equal to or greater than a threshold, as an abnormal area,
wherein the obtaining the information on the transmission amount includes:
specifying the part of the bicycle by inputting an entire image of the bicycle to a first neural network model that is trained with an image data set for each part of the bicycle to which specification information for the corresponding part of the bicycle is mapped, and
obtaining information on the transmission amount of the X-ray for the specified part by adjusting an X-ray emission position to a position of the specified part.

15. A non-transitory computer-readable storage medium including computer-executable instructions which cause, when executed by a processor, the processor to perform a non-destructive inspection method performed by a non-destructive inspection apparatus, the non-destructive inspection method comprising:
acquiring information on a transmission amount of an X-ray by emitting the X-ray to a part of a bicycle;
generating a gray scale image based on the information on the transmission amount;
measuring an amount of change in a gray value from one end to the other end of a part of the bicycle represented in the gray scale image along an extending direction of the part; and
detecting an area in which the amount of change in the gray value is equal to or greater than a threshold, as an abnormal area,
wherein the obtaining the information on the transmission amount includes:
specifying the part of the bicycle by inputting an entire image of the bicycle to a first neural network model that is trained with an image data set for each part of the bicycle to which specification information for the corresponding part of the bicycle is mapped, and
obtaining information on the transmission amount of the X-ray for the specified part by adjusting an X-ray emission position to a position of the specified part.

* * * * *